US008479598B2

(12) United States Patent
Vincent

(10) Patent No.: US 8,479,598 B2
(45) Date of Patent: Jul. 9, 2013

(54) PROBE OR SONDE FOR INVESTIGATING FLUIDS

(75) Inventor: David Robert Vincent, Ferndown (GB)

(73) Assignee: Intellitect Water Limited, Dorset (GB)

( * ) Notice: Subject to any disclaimer, the term of this patent is extended or adjusted under 35 U.S.C. 154(b) by 3 days.

(21) Appl. No.: 12/083,111

(22) PCT Filed: Oct. 17, 2006

(86) PCT No.: PCT/GB2006/003861
§ 371 (c)(1),
(2), (4) Date: Apr. 4, 2008

(87) PCT Pub. No.: WO2007/049003
PCT Pub. Date: May 3, 2007

(65) Prior Publication Data
US 2009/0158819 A1   Jun. 25, 2009

(30) Foreign Application Priority Data

Oct. 28, 2005   (GB) .................................. 0522015.7

(51) Int. Cl.
*G01D 21/00* (2006.01)
(52) U.S. Cl.
USPC ......................................... 73/866.5; 374/142
(58) Field of Classification Search
USPC ................. 73/866.5, 53.01; 374/142
See application file for complete search history.

(56) References Cited

U.S. PATENT DOCUMENTS

| 4,542,647 | A | * | 9/1985 | Molnar ....................... 73/152.54 |
| 5,233,860 | A | * | 8/1993 | Mori et al. ....................... 73/19.1 |
| 5,798,940 | A | * | 8/1998 | Bratton et al. ................. 700/267 |
| 5,821,405 | A | * | 10/1998 | Dickey et al. ................. 73/53.01 |
| 6,567,679 | B1 | | 5/2003 | Khuri et al. |
| 2002/0036136 | A1 | | 3/2002 | Kempe |
| 2003/0177851 | A1 | * | 9/2003 | Henry et al. .................. 73/866.5 |
| 2003/0233723 | A1 | * | 12/2003 | Lizotte et al. ............. 15/250.001 |
| 2005/0279532 | A1 | * | 12/2005 | Ballantyne et al. ............. 175/40 |

FOREIGN PATENT DOCUMENTS

GB              2295232 A  *  5/1996

* cited by examiner

*Primary Examiner* — Hezron E Williams
*Assistant Examiner* — Nashmiya Fayyaz
(74) *Attorney, Agent, or Firm* — Iandiorio Teska & Coleman, LLP

(57) ABSTRACT

A probe or sonde (1) comprising a plurality of sensors (3, 4, 5, 6, 8, 9, 10) for sensing different parameters, at least one sensor being mounted on or at one end of the probe or sonde (1), and at least one sensor being mounted on or at the, or one, side of the probe or sonde (1). The probe or sonde further comprises a centrally positioned stirrer (7) and in constructed from plastics discs bonded together or separated by gaskets. Sensors are used for measuring different water quality parameters, flow and temperature.

10 Claims, 3 Drawing Sheets

PROBE OR SONDE FOR INVESTIGATING FLUIDS

This invention relates to improvements in or relating to sensing apparatus and is more particularly but not exclusively concerned with sensing apparatus for sensing various parameters in the mains water supply.

Ever increasing demand on water resources, tighter quality standards, and cost reductions are persuading water supply operators to actively manage water distribution networks as a critical asset. In order to provide such management, comprehensive information on the hydraulic and quality parameters of the water is needed, creating a demand for more instrumentation. However, in order to be cost effective, generally, it would be desirable to include all the key parameter sensors, together with data collection and communication functions, in the same sensing apparatus in the form of a sensor probe. In the interests of achieving optimum flexibility and ease of use, usually, measurements made by the sensor probe must be made 'in-pipe', with no sample flow to waste or interruption to service during installation. The usual term used in the art for a multi-parameter sensor array mounted in a measurement head with common data collection facilities is a 'sonde'. Detailed considerations regarding some aspects of sonde design are discussed in U.S. Pat. No. 5,235,526, to which reference is made.

In order to maximize the number of potential installation sites, the sonde itself will often be subject to a critical maximum diameter for measurements in the afore-described scenario. This maximum diameter will usually be about 36 mm, corresponding to a minimum gate valve size of 1½ inches (3.81 cm). In order to measure the complete profile of parameters required in some scenarios, ideally, a sonde of diameter 36 mm, including the following parameters would be required:

Physical: Flow, pressure, temperature
Optical: Colour, turbidity
Chemical: Chlorine, Chloramine, dissolved oxygen, conductivity, ORP/REDOX, pH, optional Ion Selective Electrode (e.g. an ISE for fluoride).

To make the required electrochemical measurements, reference and counter electrodes may also required.

A water stirrer will usually need to be added to maintain minimum sensor flow levels in systems where the water becomes stationary e.g. overnight. Minimum sensor flow levels would need to be achieved without significantly disturbing the flow sensor.

It tends to be disadvantageous that the maximum number of sensors that can seemingly be practically mounted in the end of the sonde (an example of one such sonde is known as the In-Situ Inc. Troll 9000) is eight sensors, of about 8 mm diameter each, which apparently leaves insufficient space on the sonde for other instrumentation to measure all the parameters that may be required. The Troll 9000 is designed for environmental measurements (rivers, lakes, and so forth). It also tends to disadvantageous that, even when combining more than one parameter sensor into the same sensor body, the optical measurements tend to be difficult to make in this geometry, and the stirrer will tend to disturb the flow sensor.

It is believed that such sonde design has not been optimized and that it may be possible to construct a sonde containing sensors for measurement of e.g. the aforementioned parameters, or at least a greater number of sensors than at present, in a housing that may be much more economical to manufacture and which should be able to withstand pressures present in water distribution networks.

Water companies already measure pressure and flow at various locations in the water distribution network, and a sonde that measures other water quality parameters (the CENSAR sonde is referred to) has been available for some time, but such a sonde would seem to lack the communications and logging features necessary to become successful. The CENSAR sonde uses a single chip, incorporating a number of sensors for various measurements (including a Chlorine sensor), but a separate probe is required to measure colour and turbidity. Disadvantageously, in at least some scenarios, to install flow, pressure, turbidity and chlorine sensors at the same location would seem to require the installation of 2 probes and a flow-meter with a separate logger. Thus, the CENSAR sonde, whilst utilising unconventional technology, offers water quality parameter sensing in one sonde (the sensors are mounted in the end of the probe sonde) with optical parameter sensing being provided in another prime sonde. A steel casing is provided for the probe utilising o-rings to achieve a pressure seal.

Additionally, the Hach Company has also released a sonde for water quality measurements, but this sonde can only be used in pipes of 8" or greater diameter, which would exclude its use from all but the main distribution lines. Thus, the Hach sonde tends to be disadvantageous in that it uses conventional instrumentation in a large housing which would be unsuitable for the majority of local water distribution pipes. A stainless steel shroud surrounds the sensors that protrude from the end of the sonde.

It is an object of the present invention to provide an improved sonde or to at least alleviate the aforementioned, or other, disadvantages associated with sondes or to provide improved flow/quality parameter measurement more particularly but not exclusively in water distribution systems.

According to the present invention there is provided a sonde comprising a side wall, a first end wall at a first end of the side wall, a second end wall at a second end of the side wall, a plurality of first sensors mounted in the first end wall, a plurality of second sensors mounted in the side wall, and the sonde being such that:

(i) the first sensors extend longitudinally of the sonde;
(ii) the first sensors are positioned radially around a longitudinal axis of the sonde;
(iii) the first sensors are water quality sensors;
(iv) the second sensors extend radially outwardly from the longitudinal axis of the sonde;
(v) the sonde has a body which comprises the side wall, the first end wall and the second end wall;
(vi) the body is constructed from at least three separately formed plastics disc-shaped components which are connected together by a threaded housing which extends inside the plastics disc-shaped components, which extends along the longitudinal axis of the sonde, and which has parts which screw together to cause the threaded housing to tighten against the plastics disc-shaped components and thereby connect the plastics disc-shaped components together; and
(vii) the sonde includes an optical sensing arrangement mounted in an optical cavity in the side wall.

Said at least one sensor mounted on or at said end of the sonde may be releasably mounted so that it is replaceable and/or said sensor may be flow sensitive.

The side walling will usually be of generally circular shape (to match the diameter of pipe in which the sonde may be placed in use) and the sonde generally cylindrical, although it is possible that other sonde configurations might be feasible e.g. elliptical or polygonal.

In one embodiment of the present invention, a plurality of sensors (possibly eight) are mounted at or on said end of the sonde and, preferably, these sensors surround a (central), preferably, magnetically coupled, stirrer. The (central) stirrer is, preferably, located away or remote from the side mounted sensor or sensors, Where the sonde is to be used to measure parameters of the mains water supply, the sensors at the end of the sonde, may be (analogue) water quality sensors (e.g. to measure chemical; levels of e.g. chlorine, chloramines, dissolved oxygen, conductivity, ORP/REDOX. pH, optional Ion selective electrode e.g. an ISE for fluoride) and the side mounted sensors may be for sensing thermal mass flow. Where the side mounted sensors are thermal mass flow sensors, advantageously, the stirrer due to its location remote from the side mounted sensors, will not significantly disturb said side mounted sensors. Advantageously, a plurality of side mounted sensors measuring the same parameter may be mounted diametrically or oppositely opposed to one another in order to compensate for any misalignment of the sonde (e.g. by averaging readings) in a surrounding pipe in which measurements are taken. A temperature sensor may be side mounted on the sonde and preferably a plurality of temperature sensors may be mounted diametrically or oppositely opposed to one another (preferably in between the flow sensors) and readings e.g. averaged to compensate for any misalignment in a similar manner to the mass flow sensors.

Preferably, the sonde includes one or more optical sensors that may be for measuring water qualities such as colour and/or turbidity. The optical sensor/s is/are preferably, mounted into a cavity in one side of the sonde.

Preferably, the sensors are mounted into a body capable of withstanding 35 bars of hydrostatic pressure, which may be required in water supply parameter measurement.

Advantageously, the size of the sonde is such that it may be used in pipes of less than 8 inches (20.32 cm) in (internal) diameter and may be utilisable in pipes of only about 36 mm in (internal) diameter (and thus utilisable in pipes of 1.5 inches internal diameter). This would enable the sonde to be used in many types of water distribution systems rather than only in main distribution lines.

The sonde may have a plastics body constructed from plastics discs bonded together or separated by gaskets. Preferably, the discs are held together under compression that may be provided by a (threaded or force fit) housing for a shaft that operates the stirrer where provided as aforesaid.

The sonde may include a printed circuit board (PCB) for making electrical connections to the end-mounted sensors (e.g. to a cable loom) and preferably to achieve a seal around sensor contact/s/. For a reliable contact to the sensors, a sprung contact may be housed in the associated sensor, to reduce the amount of space required. The contact is, preferably, robust and moisture resistant.

The sonde, preferably, has data collection and/or communication functions.

Further according to the present invention there is provided a sonde having one or more of the following features;
a) one or more side mounted sensors that may be thermal mass flow sensor/s and/or optical sensor/s
b) one or more sensors in an end of the sonde with one or more side mounted sensors
c) at least one substantially radially or transverse mounted sensor preferably with at least one substantially axial or longitudinally mounted sensor
d) sensor/s as in a, b, or c in which the end or longitudinally mounted sensors are water quality sensors and the side mounted or radial/transverse sensor/s are mass flow sensors/ and or optical sensor/s,
e) sensors as in any of a) to d) having a stirrer
f) sensors preferably releasably mounted in one end of the sonde, preferably of a length down to about 15 mm and preferably of width down to about 8 mm and/or having mechanical means to correctly orient the sensor and/or mechanical means to ensure the correct type of sensor in an associated receiving hole/recess
g) a housing of plastics preferably constructed of discs under compression
h) a measurement head of 36 mm diameter and preferably including water flow and/or quality and/or optical sensor/s
i) at least one substantially axially or longitudinally or end mounted sensor which is releasably mounted to the sonde so that it is replaceable.

Further according to the present invention there is provided a through flow cell including a sonde as defined in any one of the preceding statements of invention.

Further according to the present invention there is provided a water distribution network including a plurality of sondes as defined in any one of the preceding statements of invention arranged to provide measurement information at different locations within the network.

Many other advantageous features of the sonde will be apparent from the following description and drawings.

An embodiment of a sonde will now be described, by way of example only, with reference to the accompanying much simplified drawings in which.

Figure 1:
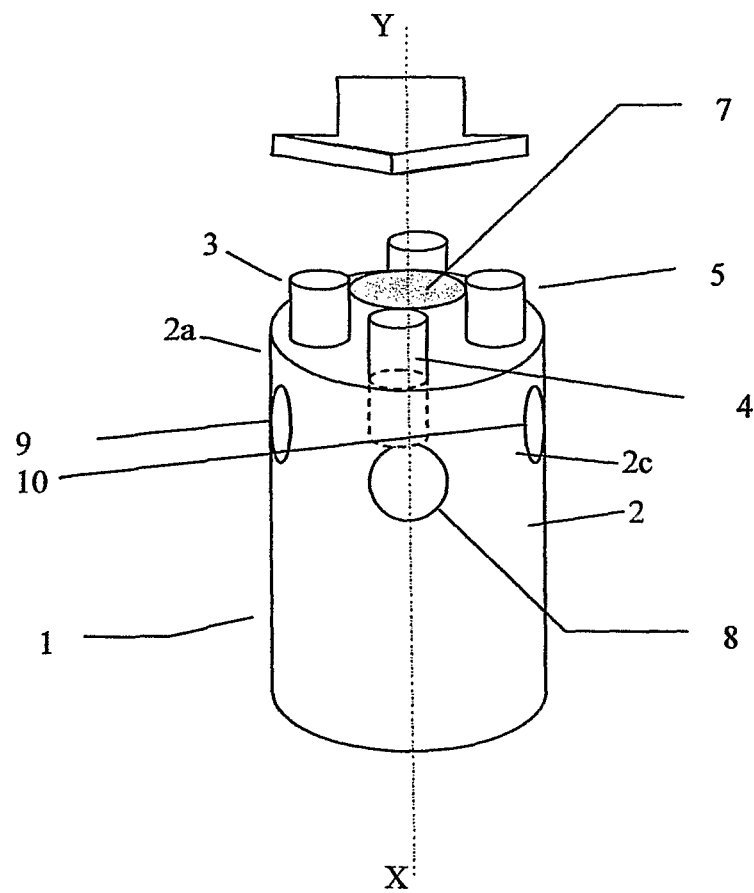
FIG. 1 shows diagrammatically in perspective view, the relative disposition of sensors in the sonde.

Referring to the FIG. 1 of the drawings, a sonde 1 has a measurement head 2 which is generally cylindrical in form and includes four, longitudinally or axially mounted, replaceable, water quality sensors 3,4,5,6 at and projecting from, an upper end 2a of the measurement head 2. Whilst only four sensors are shown in FIG. 1 of the drawings, this is for ease of illustration only, since in practice the measurement head will usually be provided with eight such, equi-angularly spaced, sensors. The sensors 3,4,5,6 are mounted in, and project from, end wall 2b and are equi-angularly spaced about the axis X of the measurement head 2 and about a central stirrer 7, in the form of a spinning disc although other stirrer configurations are possible and the stirrer could e.g. be provided with fins. Advantageously, additional, transverse or radially mounted sensors 8,9,10 are mounted in the, side walling 2c of the measurement head 2 below the sensors 3,4,5,6 as should be apparent from FIG. 1. Sensors 9 and 10 are diametrically opposed thermal mass flow sensors. Sensor 8 is a water temperature sensor and, although not shown in the drawings, a second such sensor 8 may be positioned diametrically opposed to the first sensor 8. Thus, the four sensors 8,8,9,10 are equi-angularly spaced around the side walling 2c.

Advantageously, the combination of axial 3,4,5,6 and radial 8,9,10 sensors in the measurement head 2 allows a much more compact design of sonde (of only 36 mm diameter) than if all the sensors were to be mounted longitudinally of the measurement head, as in known arrangements.

In this instance, the probe/sonde is utilisable to measure water flow (the water flow is indicated as out of the paper, by arrow Y, in FIG. 1) and quality parameters 'in-pipe' in a mains water supply distribution network, in a manner to be described.

All the parameters that need to be measured in such a water supply distribution network are provided on the small measurement head 2, with any anomolous effects of the stirrer 7 being isolated from the thermal mass flow sensors 9,10 since the sensors 9,10 are remote from the stirrer 7. If the thermal mass flow sensors 9,10 were positioned on the end wall 2*b*, the stirrer could interfere with or disturb the measurements taken.

1) Flow measurement:

The thermal mass flow sensors 9,10 are fitted into the side walling 2*a* of the sonde 1 away from the stirrer 7. The disposition of diametrically opposed sensors 9,10 and inclusion of temperature sensors 8 of the same construction mounted in a similar diametrically opposed arrangement in between sensors 9,10 enables flow measurements to be taken using simple circuitry.

It is also believed that the shape and size of the sonde 1 will reduce the effects of turbulent flow, and e.g. by averaging the outputs of the flow sensors 9,10 mounted diametrically opposed to one another on each side of the measurement head 2, it will be possible to compensate or adjust for poor alignment of the sonde in the pipe where measurements are being taken Thus, advantageously, the thermal mass flow sensors 9,10 have been mounted in the body of the sonde 1 in such manner as create space for other sensors in a unique manner. The sonde 1 may be contained in a flow-through cell (not shown).

Figure 2A:
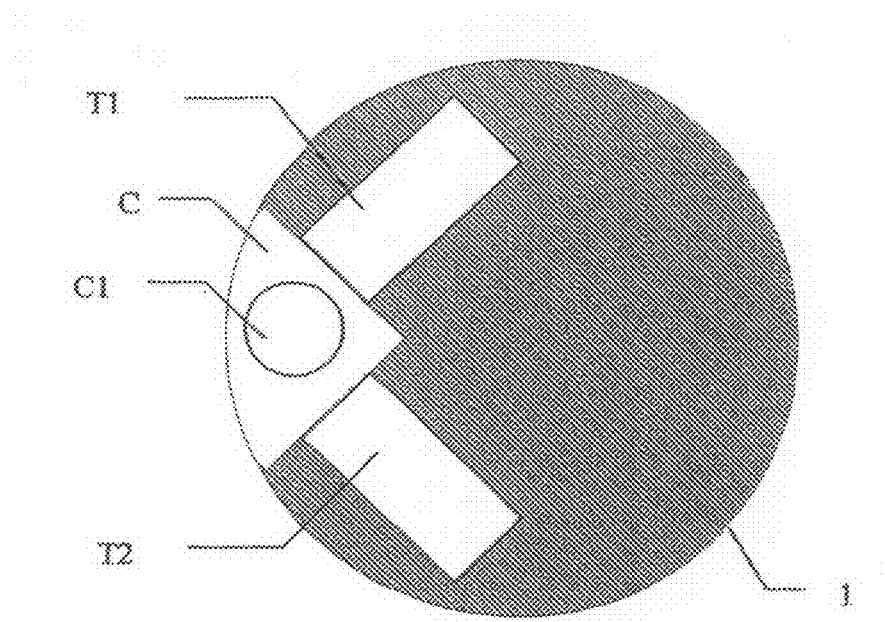
FIG. 2a shows diagrammatically a sectional plan view of the sonde body.
Figure 2B:
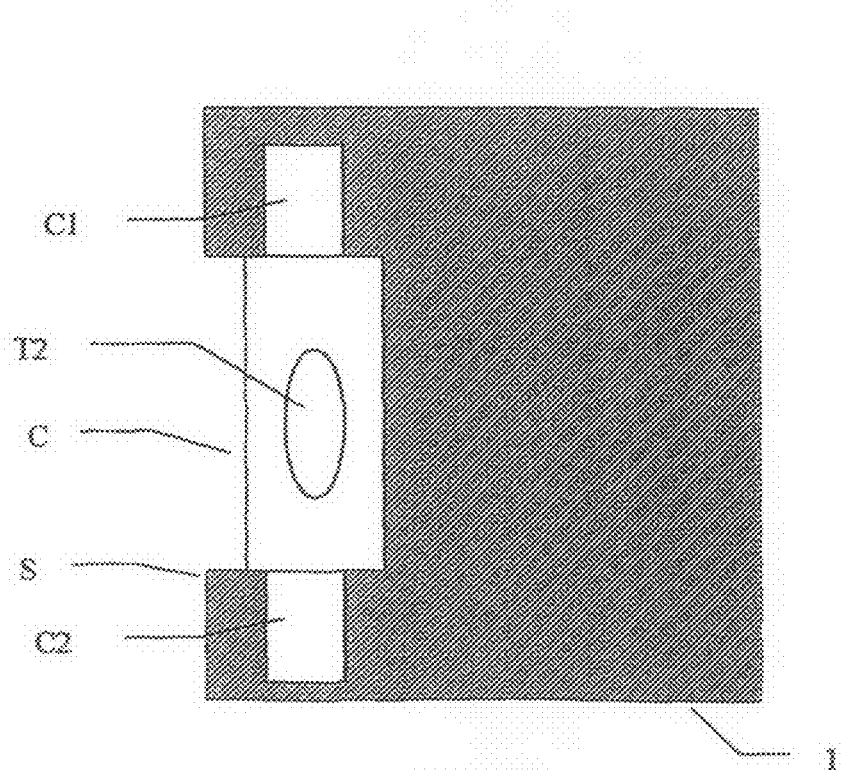
FIG. 2b shows diagrammatically a sectional side view of the sonde body.

2) Water quality (Optical) measurements:

For convenience, colour and turbidity sensing arrangements in the sonde 1 have been omitted from the diagrammatic arrangement In FIG. 1. FIGS. 2*a* and 2*b* show a lower section of the sonde body 1 illustrating the optical sensing arrangements. Colour and turbidity sensing each require a source c1,t1 and a detector c2,t2 (at 180 degrees and 90 degrees to each other respectively as shown in FIGS. 2*a*,2*b*). The source and detector need to be positioned to minimise scatter from the inside of the pipe-not shown-(for turbidity measurement) and to maximise the path length (for colour measurement). Traditionally, it is difficult to take adequate measurements for these parameters from small sensors protruding from the end of the sonde. However, advantageously, by making the water quality sensors 3,4,5,6 as short as possible e.g. 15 mm long and 8 mm diameter (as shown in FIG. 2), there is space inside the sonde 1 body to fit optical components, arranged about an optical cavity C built into one side S of the sonde. In summary, it is believed the configuration of optical sensors with water quality sensors in the same body as shown in FIG. 2 is highly advantageous. Directing optical components upstream may provide some anti-fouling advantage since there would be no boundary layer associated with flow parallel to the surface, therefore resulting in reduced bio-film deposition.

3) Construction:

All the afore-described sensors 3,4,5,6,8,8,9,10,c1,c2,t1, t2, for applications in measuring water supply parameters, usually need to be sealed into a body that will withstand 35 bars of hydrostatic pressure. Electrical connections are needed to the sensors 3,4,5,6,8,8,9,10, c1,c2,t1,t2, and the recesses or holes for the, releasably mounted, replaceable sensors 3,4,5,6 (water quality) need to be sealed from each other, as well as being water tight when not occupied. Traditionally, a metal housing around a plastics body incorporating o-ring seals would be used. Sealing a plastics body inside a metal casing with apertures in the side would be problematic, and also would reduce the useable diameter of the probe/sonde by the thickness of the metal housing.

Figure 3:
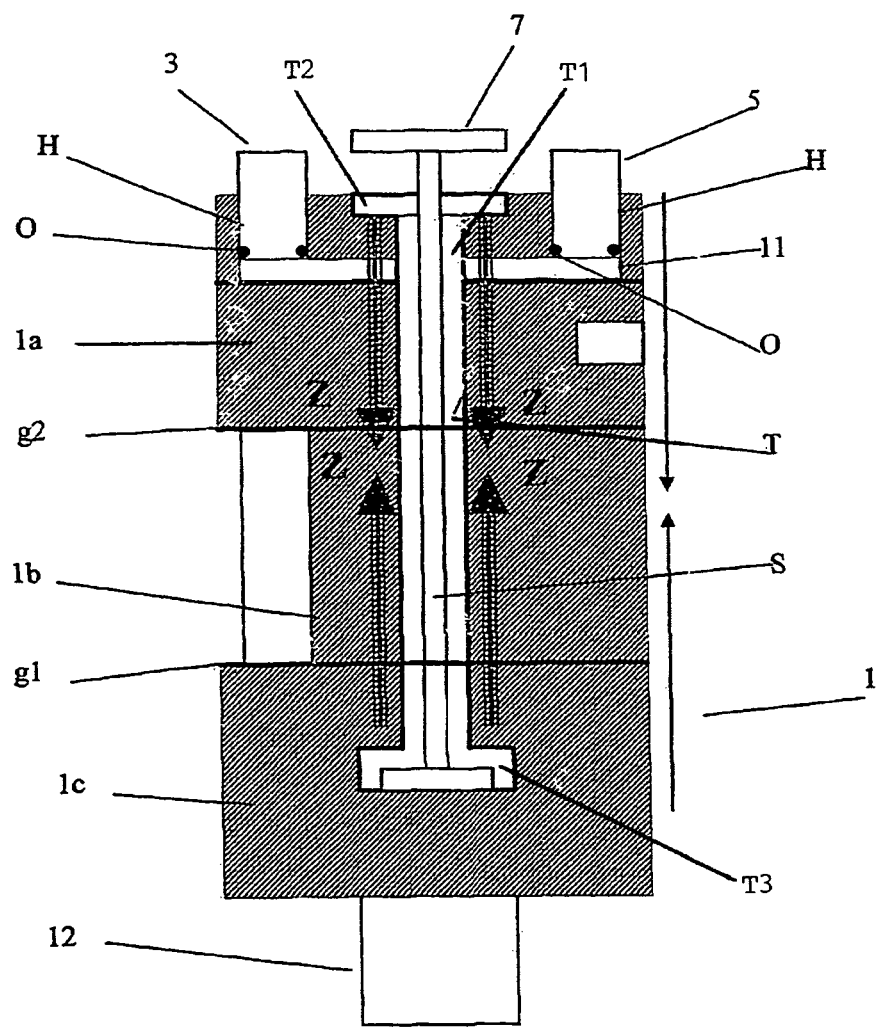
FIG. 3 shows a cross-sectional side view of the sonde.

Advantageously, in accordance with this embodiment of the present invention and as shown in FIG. 3 of the drawings, the probe/sonde 1 is constructed from a stack of three, generally cylindrical hard plastics components 1*a*,1*b*,1*c*, either bonded together or separated by a compressed gaskets g1,g2, with no outer shell or housing provided. This construction enables the inclusion of levels of components inside the probe/sonde (for example, a PCB 11 for making connections to the sensors).

In order to make reliable contacts to the replaceable sensors 3,4,5,6, it would be usual to use a sprung contact, mounted in the body of the sonde 1.

However, to reduce the space required, this sprung contact (not shown) is housed in the sensor 3,4,5,6, with a more robust (moisture resistant) contact mounted onto the contact PCB 11. PCB 11 connects sensors 3,4,5,6 on one side with a connector to cable loom (not shown) on the other.

Advantageously, sensor housing H is sealed to PCB 11 to prevent leaks even when not occupied. O-rings O are positioned to minimise air entrapment when inserting new, replacement, sensors 3,4,5,6 into the associated housing H and the sensor 3,4,5,6 is mechanically retained to the bottom of the sensor housing IL Advantageously, the sensor 3,4,5,6 may have mechanical means (the bottom of the sensor may be keyed) to ensure the correct orientation of the electrical connections to the sensor and/or insertion of the correct type of sensor into the receiving hole/recess. The mechanical means is not shown in the FIGURES of the drawings.

The stacked components 1*a*, 1*b*, 1*c* are compressed together by a threaded stirrer shaft housing T. The housing T comprises a tubular portion T1, a transverse portion T2, and a transverse portion T3. The housing T thus has the form of a hollow nut and bolt. One of the transverse portions T2, T3 is threaded to enable the transverse portions T2, T3 to be tightened towards each other to pull the components 1*a*, 1*b*, 1*c* together as indicated by the arrows Z. Shaft S for the stirrer 7 extends centrally of the sonde 1 and extends through all three components 1*a*, 1*b*, 1*c*. The shaft S is positioned in the housing T as shown. The stirrer 7 is magnetically coupled at the bottom to a motor magnet 7*a* for driving the stirrer. Advantageously, such magnet coupling eliminates the need for mechanical seals around the a moving shaft of the stirrer 7. Advantageously, the stirrer 7 itself may be used to generate power (power scavenging). At the bottom of the sonde 1 is a shaft 12 that holds the sonde 1 in the water.

To Summarise:—

To solve the problem of mounting a large number of sensors into a small volume, advantageously, in the embodiment of the present invention as afore-described , the side/s of the sonde are used as well as the end for mounting sensors. The sonde design thus has the following advantageous features:

1) Thermal flow sensors mounted in the side/s of the sonde. To obviate any problem in measurement that could require a precise alignment of the sonde head with the direction of flow to achieve reasonable accuracy, a flow sensor is placed on each side of the sonde, to compensate for any inaccuracy in measurement due to misalignment (by averaging sensor readings). The size and shape of the sonde head, and the use of dual sensors measuring the same parameter, may also compensate for turbulent flow effects.

2) Optical sensors (for colour and turbidity) are mounted into a cavity in the side of the sonde. Traditionally, these sensors are usually incorporated either in a single parameter sensor instrument, or as individual sensors in the end of the device. In the embodiment of the present invention as afore-described, these sensors are mounted in the side of the sonde (upstream) to make space for other sensors in the sonde end.

3) Adequate sealing and assembly of the sonde is achieved by compressing sections together centrally, instead of containing the sensor in a metal housing. Plastics appropriate for this task include, but are not limited to, PEEK and Vectra (liquid crystal polymer, which may be mineral filled). Printed Circuit Boards (PCBs) are used to connect sensors to cable looms and achieve a seal around the replaceable sensor contacts.

It is to be understood that the scope of the present invention is not to be unduly limited by the particular choice of terminology and that a specific term may be replaced or supplemented by an equivalent or generic term. Thus for example, the sonde may alternatively be referred to as a probe. The present invention may include multi-probed metering apparatus including at least one sonde. The singular may include the plural and vice versa. Additionally, any range mentioned herein for any parameter or variable shall be taken to include a disclosure of any derivable sub-range within that range or of any particular value of the variable or parameter arranged within, or at an end of, the range or sub-range.

The invention claimed is:

1. A sonde comprising a side wall, a first end wall at a first end of the side wall, a second end wall at a second end of the side wall, a plurality of first sensors mounted in the first end wall, a plurality of second sensors mounted in the side wall, and the sonde being such that:
   (i) the first sensors extend longitudinally of the sonde;
   (ii) the first sensors are positioned radially around a longitudinal axis of the sonde;
   (iii) the first sensors are water quality sensors;
   (iv) the second sensors extend radially outwardly from the longitudinal axis of the sonde;
   (v) the sonde has a body which comprises the side wall, the first end wall and the second end wall;
   (vi) the body is constructed from at least three separately formed plastics disc-shaped components which are connected together by a threaded housing which extends inside the plastics disc-shaped components, which extends along the longitudinal axis of the sonde, and which has parts which screw together to cause the threaded housing to tighten against the plastics disc-shaped components and thereby connect the plastics disc-shaped components together; and
   (vii) the sonde includes an optical sensing arrangement mounted in an optical cavity in the side wall.

2. A sonde according to claim 1 and including a stirrer.

3. A sonde according to claim 2 in which the stirrer is a magnetically coupled stirrer.

4. A sonde according to claim 2 in which the stirrer is mounted in the first end, and in which the stirrer extends along the longitudinal axis of the sonde.

5. A sonde according to claim 1 in which the second sensors include two diametrically opposed thermal mass flow sensors, and at least one water temperature sensor.

6. A sonde according to claim 1 in which the first sensors connect to a printed circuit board which is positioned in the sonde and which extends across the sonde transversely to the longitudinal axis of the sonde.

7. A through flow cell including a sonde according to claim 1.

8. A water distribution network including a plurality of sondes according to claim 1 and arranged to provide measurement information at different locations within the network.

9. A sonde according to claim 1 and including a turbidity sensing arrangement which is mounted in the side wall.

10. A sonde according to claim 1 in which the plastics disc-shaped components are bonded together or separated by compressed gaskets.

* * * * *